United States Patent [19]
Darcey et al.

[11] Patent Number: 6,126,622
[45] Date of Patent: Oct. 3, 2000

[54] MEDICAL SPLINT PRODUCT

[75] Inventors: Thomas D. Darcey, Mooresville; Ronald L. Kelley, Huntersville; David C. Carpenter, Sparta, all of N.C.

[73] Assignee: Smith & Nephew, Inc., Charlotte, N.C.

[21] Appl. No.: 08/827,164

[22] Filed: Mar. 27, 1997

[51] Int. Cl.⁷ ...................................................... A61F 5/00
[52] U.S. Cl. .............................................................. 602/5
[58] Field of Search ................................................... 602/5

[56] References Cited

U.S. PATENT DOCUMENTS

| | | |
|---|---|---|
| 4,235,228 | 11/1980 | Gaylord, Jr. et al. . |
| 4,442,833 | 4/1984 | Dahlen et al. . |
| 4,502,479 | 3/1965 | Garwood et al. . |
| 4,770,299 | 9/1988 | Parker . |
| 4,869,046 | 9/1989 | Parker . |
| 4,899,738 | 2/1990 | Parker . |
| 5,003,970 | 4/1991 | Parker et al. . |
| 5,454,780 | 10/1995 | Duback et al. . |
| 6,042,557 | 3/2000 | Ferguson et al. ........................ 602/6 |

*Primary Examiner*—Mark O. Polutta
*Attorney, Agent, or Firm*—Adams, Schwartz & Evans, P.A.

[57] ABSTRACT

An elongate medical splint product is provided for being dispensed in lengths suitable for a given medical use. The splint product includes a multi-layer moisture-hardenable plaster substrate having first and second opposed major surfaces. A soft foam cushion envelopes the first major surface and opposed marginal portions of the second major surface of the substrate. A moisture absorbent panel overlies opposed marginal portions of the second major surface of the substrate and the cushion. First and second spaced-apart rows of stitches extend along the length of the splint product and through the marginal portions of the substrate, the foam cushion, and the panel to bind the substrate, cushion, and panel together. This forms a unitary bandaging product which can be dispensed, cut to length, and applied without further assembly.

10 Claims, 6 Drawing Sheets

MEDICAL SPLINT PRODUCT

TECHNICAL FIELD AND BACKGROUND OF THE INVENTION

This invention relates to a medical splint product for treating injuries, such as broken bones, requiring immobilization of a body part. The invention is sufficiently flexible for packaging in roll form prior to use, and is conveniently dispensed and cut to any desired length to custom-fit the patient. After dispensing and cutting, the splint is dipped in a water bath, and rolled and squeezed in a dry towel to remove excess water. The splint is then formed around the injured body part, and wrapped with bandaging to hold the splint in place as it hardens.

Conventional practice has been to fabricate a cast or splint upon an injured limb by initially applying to the limb a protective covering of cotton fabric or the like and then overwrapping the covering and limb with a woven cloth impregnated with plaster of paris which has been wetted by dipping in water immediately prior to application. This practice is still in widespread use but possesses several significant disadvantages. For example, the above-described application procedure is messy and time consuming. Several components are required and considerable skill is necessary.

The present invention addresses these and other problems of the prior art by providing a unitary medical splint product which is conveniently stored in roll form, dispensed, cut to any desired length, and applied without further assembly. The invention includes multiple overlying layers of plaster as a unitary substrate, and spaced-apart rows of stitching extending along the length of the splint and through the plaster layers from one major surface of the splint to the other. The stitching binds the splint together, and prevents the plaster layers from shifting or migrating as the splint is wetted and applied to the patient. The stitching further ensures a smoother plaster surface, minimized plaster loss, and promotes uniform lamination of the plaster layers and increased strength.

SUMMARY OF THE INVENTION

Therefore, it is an object of the invention to provide a unitary medical splint product which can be conveniently stored in roll form, dispensed, cut to any desired length, and applied without further assembly.

It is another object of the invention to provide a splint product which is sufficiently flexible for packaging in roll form prior to use.

It is another object of the invention to provide a splint product which includes multiple overlying layers of plaster, and spaced-apart rows of stitching extending along the length of the splint and through the plaster layers from one major surface of the splint to the other.

It is another object of the invention to provide a splint product including plaster layers which will not shift or migrate as the splint is wetted and applied to the patient.

It is another object of the invention to provide a splint product which has a smooth plaster surface.

It is another object of the invention to provide a splint product which yields minimal plaster loss during and after application.

It is another object of the invention to provide a splint product which promotes uniform lamination of the plaster layers and increased strength.

These and other objects of the present invention are achieved in the preferred embodiments disclosed below by providing an elongate medical splint product for being dispensed in lengths suitable for a given medical use. The splint product includes a multilayer moisture-hardenable plaster substrate having first and second opposed major surfaces. A soft foam cushion envelopes the first major surface and opposed marginal portions of the second major surface of the substrate. A moisture absorbent panel overlies opposed marginal portions of the second major surface of the substrate and the cushion. First and second spaced-apart rows of stitches extend along the length of the splint product and through the marginal portions of the substrate, the foam cushion, and the panel to bind the substrate, cushion, and panel together. This forms a unitary bandaging product which can be dispensed, cut to length, and applied without further assembly.

According to one preferred embodiment of the invention, the foam cushion is folded to define spaced-apart opposed marginal portions overlying the marginal portions of the second major surface of the substrate. The marginal portions of the foam cushion cooperate to form a centrally disposed moisture-transfer channel therebetween. An absorbent panel overlies the moisture-transfer channel and contacts the substrate to absorb and wick moisture away from the substrate.

According to another preferred embodiment of the invention, a row of center stitches extends along the length of the splint product through the absorbent panel and substrate in an area of the moisture-transfer channel for attaching the panel directly to the substrate.

According to yet another preferred embodiment of the invention, the substrate includes a plurality of knitted or woven fabric layers.

According to yet another preferred embodiment of the invention, the moisture absorbent panel includes cotton fibers.

According to yet another preferred embodiment of the invention, the foam cushion is relatively thick as compared to the fabric panel.

According to yet another preferred embodiment of the invention, the cushion is an elongate tubular sleeve enveloping the first and second major surfaces and opposed marginal portions of the substrate.

According to yet another preferred embodiment of the invention, the width of the moisture absorbent panel is less than the width of the substrate.

According to yet another preferred embodiment of the invention, the splint product is sufficiently flexible for packaging in roll form.

BRIEF DESCRIPTION OF THE DRAWINGS

Some of the objects of the invention have been set forth above. Other objects and advantages of the invention will appear as the description proceeds when taken in conjunction with the following drawings, in which.

DESCRIPTION OF THE PREFERRED EMBODIMENT AND BEST MODE

Figure 1:
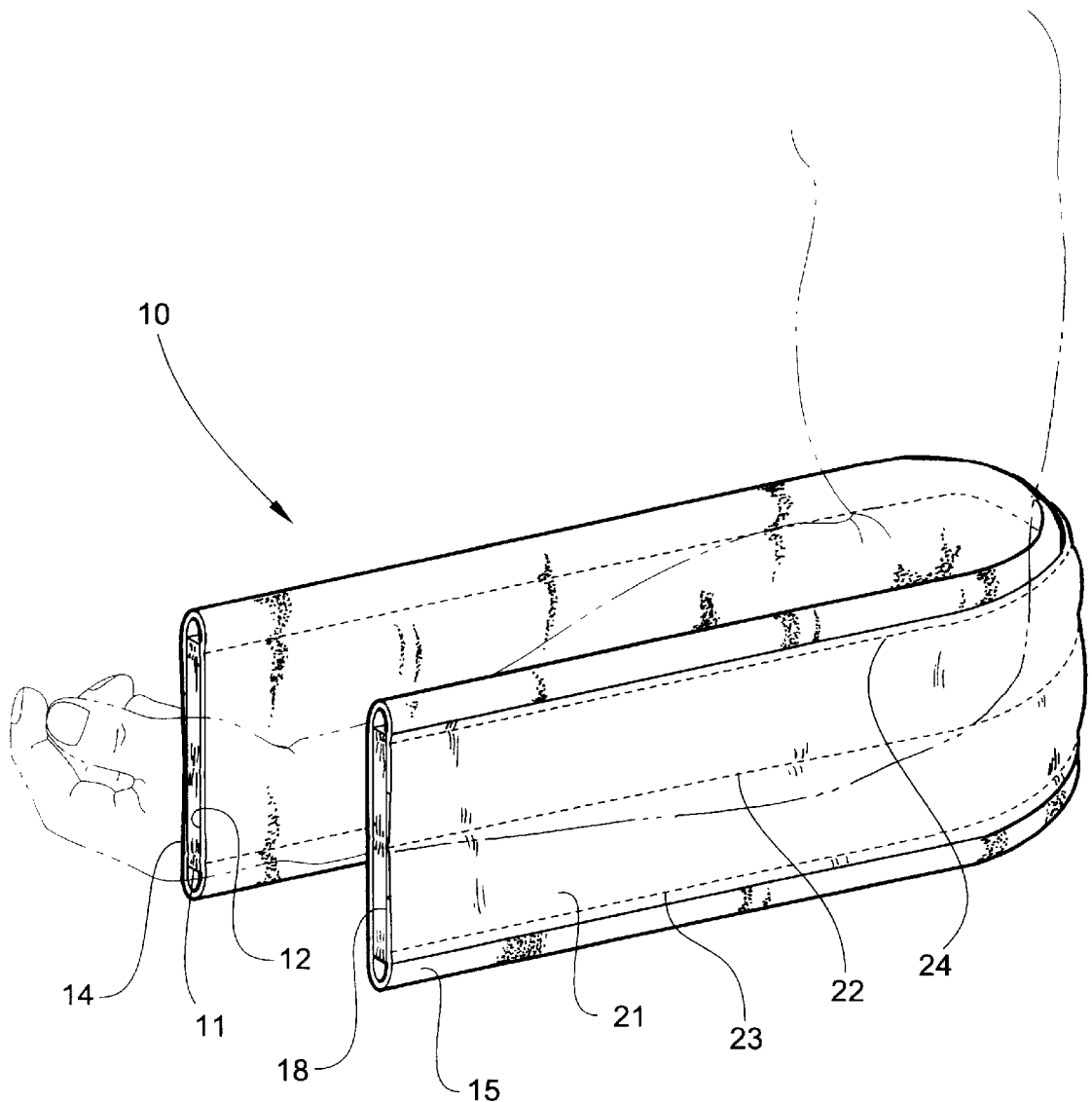
FIG. 1 is a perspective view of the splint product according to one preferred embodiment in the process of being applied to the arm of a patient.

Referring now specifically to the drawings, a medical splint product according to the present invention is illustrated in FIG. 1 and shown generally at reference numeral 10. The splint product 10 is preferably packaged in roll form, and conveniently dispensed and cut to any desired length to custom-fit the patient. Alternatively, the splint product 10 may be folded in overlapping lengths of a preferred dimension to fit within a dispenser, or pre-cut to standard lengths and packaged.

After dispensing and cutting, the length of splint product 10 is dipped in a water bath, and rolled and squeezed in a dry towel to remove excess water. The splint product 10 is then formed around the injured body part, and wrapped with bandaging to the product in place as it hardens. Preferably, the splint product 10 sets in about 4–6 minutes and cures in about 24 hours. The splint product 10 may be made in a variety of sizes, such as 2-inch, 3-inch, 4-inch, 5-inch, or 6-inch widths.

Figure 2:
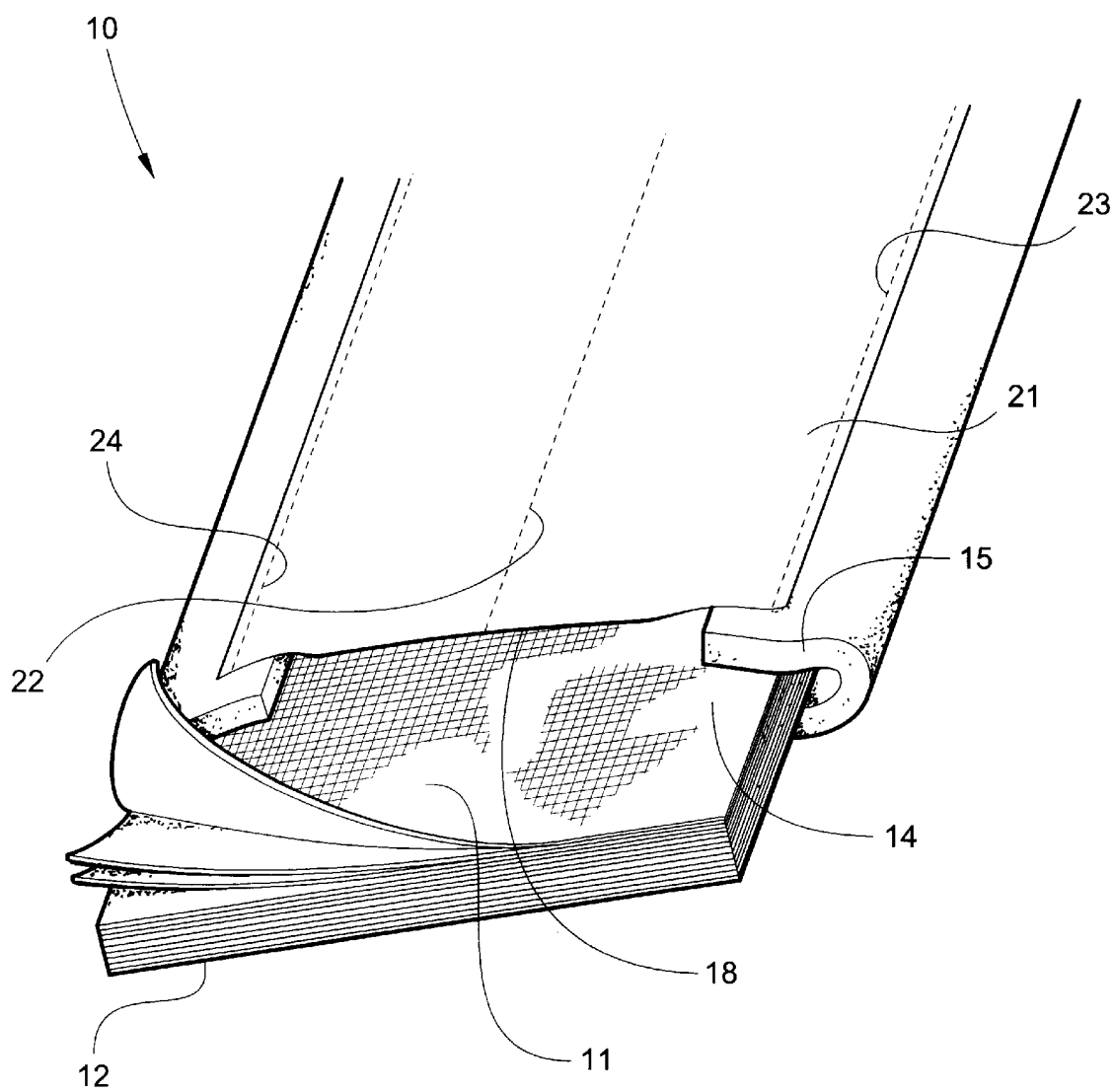
FIG. 2 is a fragmentary perspective view of the splint product with layers of the substrate peeled back.
Figure 3:
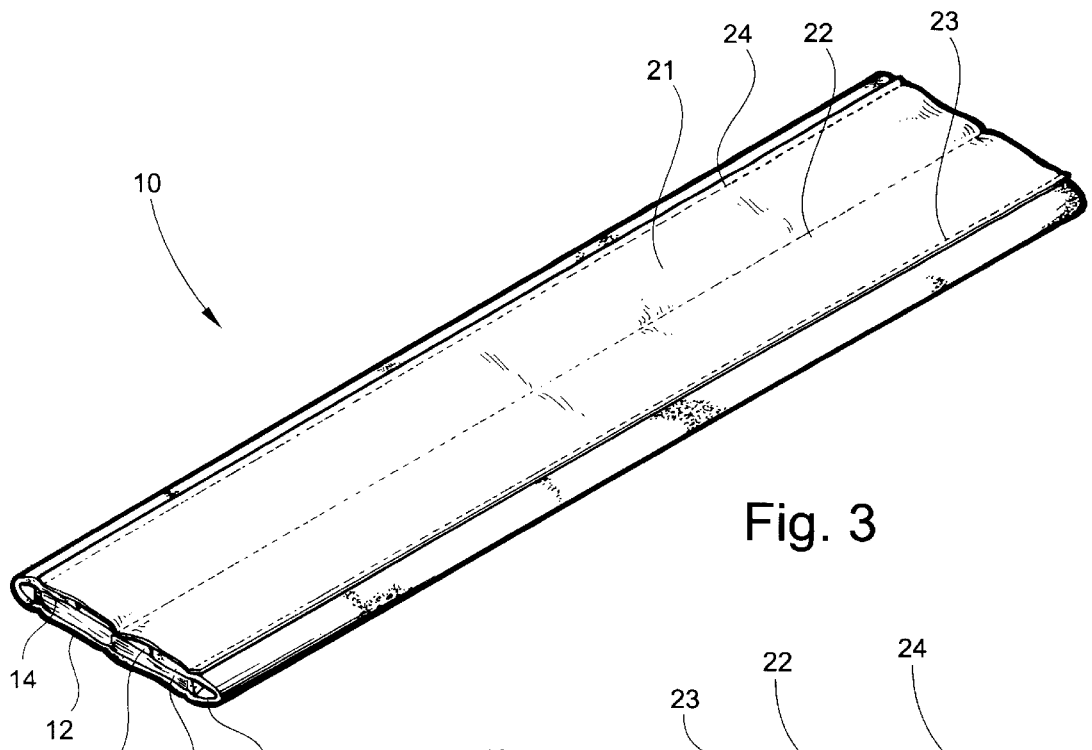
FIG. 3 is a perspective view of the splint product laid flat and showing the outside surface of the splint product which resides away from the skin of the patient.
Figure 4:
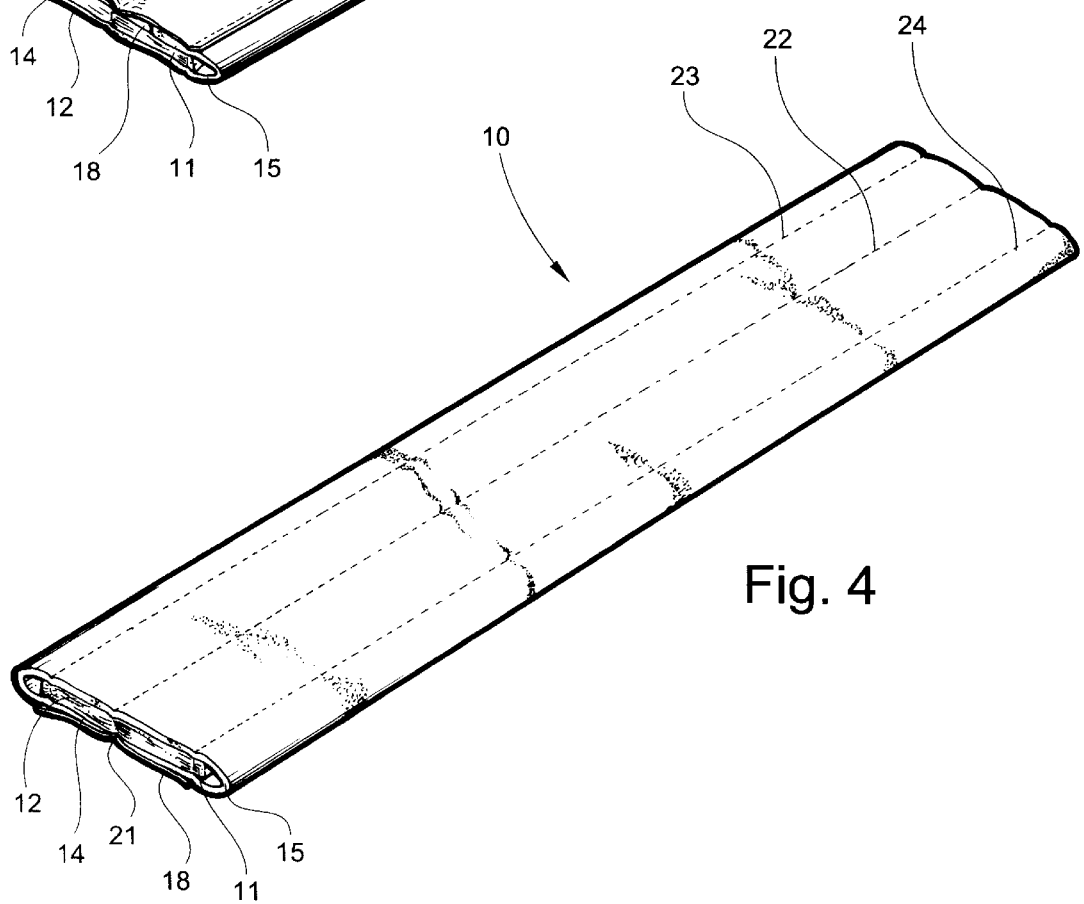
FIG. 4 is a perspective view of the splint product laid flat and showing the inside surface of the splint product which resides next to the skin of the patient.
Figure 5:
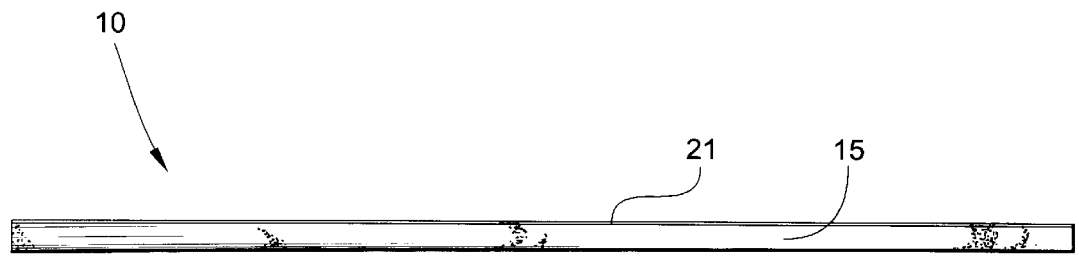
FIG. 5 is a side elevational view of the splint product.

As best shown in FIGS. 2–4, the splint product 10 is formed of a multi-layer moisture-hardenable substrate 11 including plaster of paris and having an inside major surface 12 which faces the skin of the patient and an outside major surface 14 facing away from the patient. The plaster substrate 11 preferably includes between 10 and 20 overlying layers of knitted or woven, relatively open-mesh fabric coated with fast-setting plaster of paris. According to one embodiment, the splint product 10 incorporates a plaster substrate manufactured by Smith & Nephew, Inc., and sold under the trademark "Gypsona".

A soft foam cushion 15 envelopes the inside major surface 12 and opposed marginal portions of the outside major surface 14 of the plaster substrate 11 to provide a comfortable, cushioning barrier between the substrate 11 and the skin of the patient. The cushion 15 shields any sharp edges of the substrate 11 from the patient, and limits shifting of the splint product 10 on the body part. Preferably, the foam cushion 15 is about ¼ inch thick, and is formed of a flexible non-reticulated polyurethane foam which is non-allergenic.

The marginal portions of the foam cushion 15 overlying the outside major surface 14 of the substrate 11 cooperate to form a centrally-disposed moisture transfer channel 18 extending longitudinally from one end of the splint product 10 to the other. A moisture absorbent panel 21 overlies the channel 18 and the marginal portions of the cushion 15 to rapidly absorb and wick moisture away from the substrate 11, thereby increasing its set and cure time. The panel 21 is formed of a fabric including highly-absorbent hydrophilic fibers, such as cotton. The panel 21 is preferably formed of cotton flannel with a raised nap.

According to one embodiment, a center row of stitches 22 extends along the length of the splint product 10 through the absorbent panel 21 and substrate 11 in an area of the moisture transfer channel 18 for attaching the panel 21 directly to the substrate 11. The capillary action of the absorbent panel fibers draws moisture outwardly from the substrate 11 where it rapidly dissipates over the surface area of the panel 21. The width of the moisture absorbent panel 21 is greater than the width of the channel 18 and preferably less than the width of the substrate 11.

Figure 6:
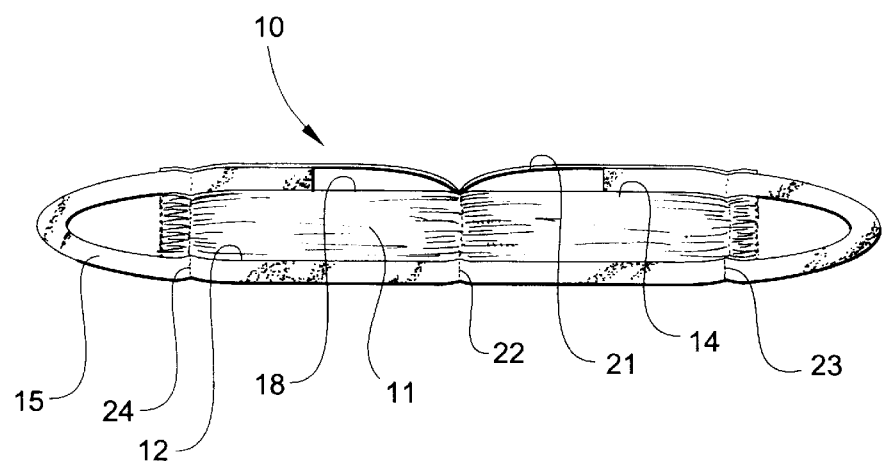
FIG. 6 is an end elevational view of the splint product.

As best shown in FIG. 6, first and second spaced-apart side rows of stitches 23 and 24 extend along the length of the splint product 10 and through the marginal portions of the substrate 11, the foam cushion 15, and the panel 21 to bind the substrate 11, cushion 15, and panel 21 together to form a unitary bandaging product suitable for use without any further assembly. The multiple rows of stitches 22, 23, and 24 extend completely through the splint product 10 from one side to the other.

Figure 7:
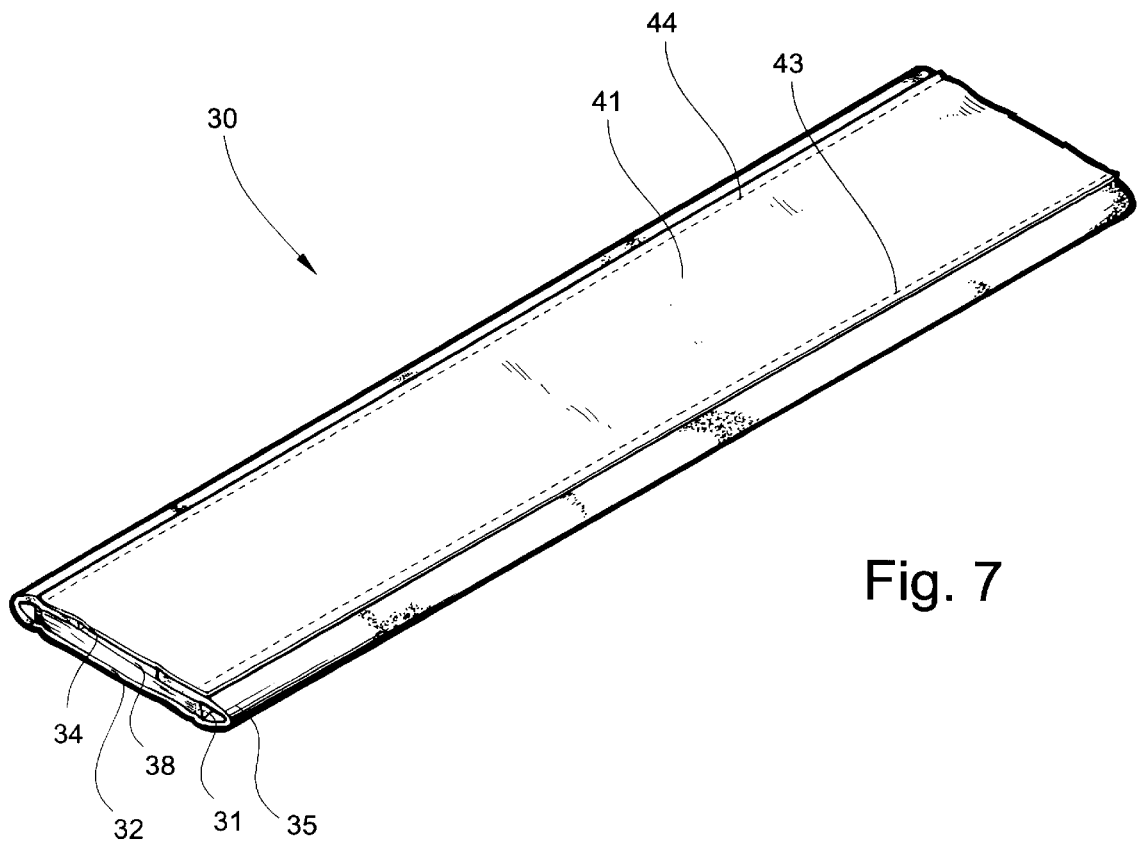
FIG. 7 is a perspective view of a splint product according to a second preferred embodiment of the invention, and showing the outside surface of the splint product which resides away from the skin of the patient.
Figure 8:
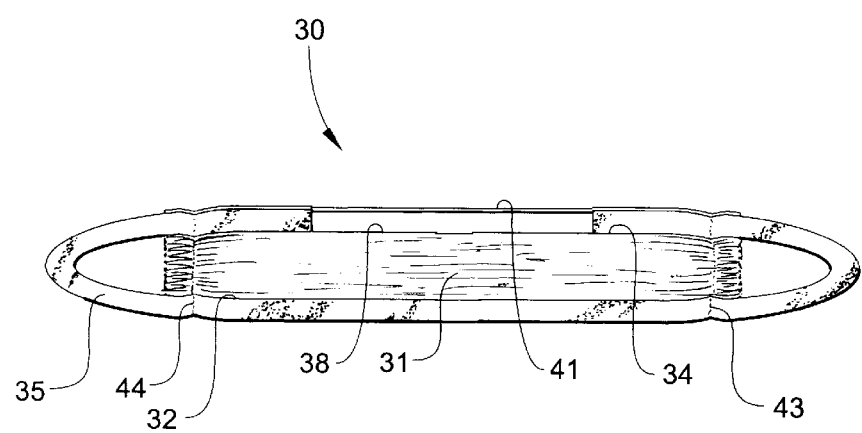
FIG. 8 is an end elevational view of the splint product shown in FIG. 7.

An alternative embodiment of a splint product 30 according to the invention is illustrated in FIGS. 7 and 8. The splint product 30 is formed of a multi-layer, moisture-hardenable substrate 31 having an inside major surface 32 which faces the skin of the patient and an outside major surface 34 facing away from the patient. A soft foam cushion 35 envelopes the inside major surface 32 and opposed marginal portions of the outside major surface 34 to provide a comfortable, cushioning barrier between the substrate 31 and the skin of the patient.

The marginal portions of the foam cushion 35 overlying the outside major surface 34 of the substrate 31 cooperate to form a centrally-disposed moisture transfer channel 38 extending longitudinally from one end of the splint product 30 to the other. A moisture absorbent panel 41 overlies the channel 38 and the marginal portions of the cushion 35 to rapidly absorb and wick moisture away from the substrate 31. The panel 41 is formed of highly-absorbent hydrophilic fibers, such as cotton.

First and second spaced-apart side rows of stitches 43 and 44 extend along the length of the splint product 30 and through the marginal portions of the substrate 31, the foam cushion 35, and the panel 41 to bind the substrate 31, cushion 35, and panel 41 together to form a unitary bandaging product suitable for use without any further assembly. The side rows of stitches 43 and 44 extend completely through the splint product 30 from one side to the other.

Unlike the splint product 10, the splint product 30 does not include a center row of stitches. This embodiment is particularly applicable to smaller product sizes, such as the 2-inch and 3-inch width sizes.

Figure 9:
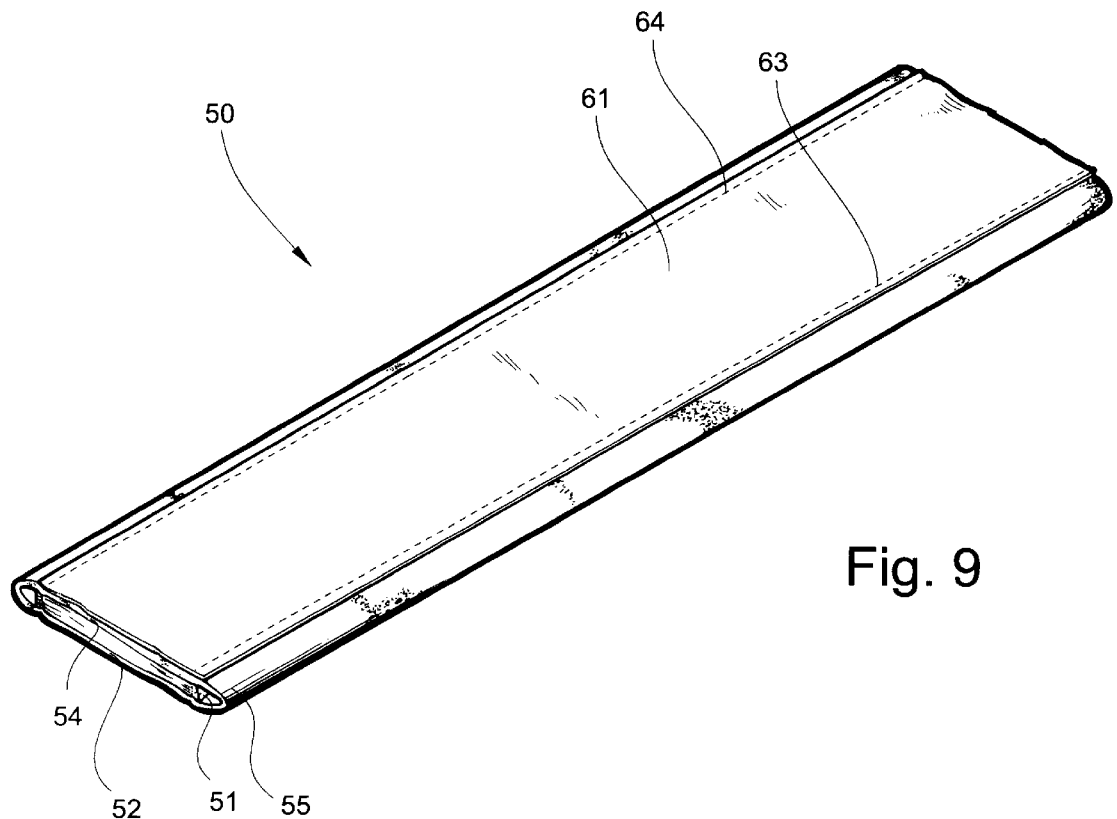
FIG. 9 is a perspective view of a splint product according to a third preferred embodiment of the invention, and showing the outside surface of the splint product which resides away from the skin of the patient.
Figure 10:
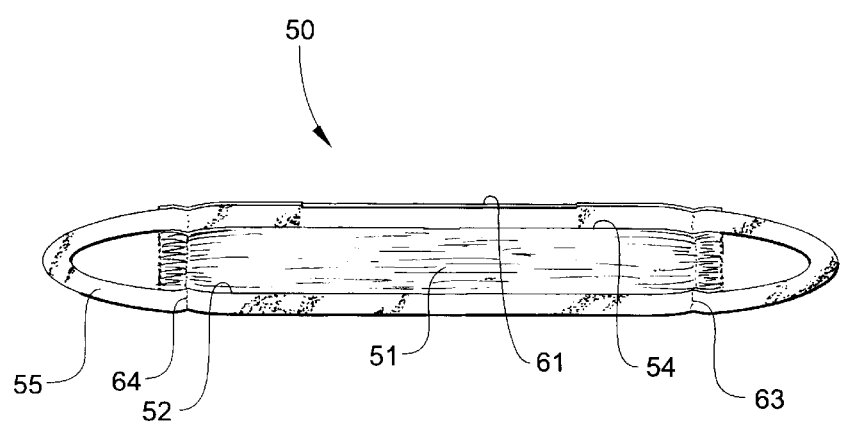
FIG. 10 is an end elevational view of the splint product shown in FIG. 9.

A further alternative embodiment of a splint product 50 according to the invention is illustrated in FIGS. 9 and 10. The splint product 50 is formed of a multi-layer, moisture-hardenable substrate 51 having an inside major surface 52 which faces the skin of the patient and an outside major surface 54 facing away from the patient. A soft foam cushion sleeve 55 surrounds the inside and outside major surfaces 52 and 54 to provide a comfortable, cushioning barrier between the substrate 51 and the skin of the patient.

A moisture absorbent panel 61 overlies the portion of the cushion sleeve 55 adjacent the outside major surface 54 of the substrate 51 to rapidly absorb and wick moisture away from the substrate 51, thereby increasing its set and cure time. The panel 61 is formed of highly-absorbent hydrophilic fibers, such as cotton.

First and second spaced-apart side rows of stitches 63 and 64 extend along the length of the splint product 50 and through the marginal portions of the substrate 51, the foam cushion 55, and the panel 61 to bind the substrate 51, cushion 55, and panel 61 together to form a unitary bandaging product suitable for use without any further assembly. The side rows of stitches 63 and 64 extend completely through the splint product 50 from one side to the other.

A medical splint product is described above. Various details of the invention may be changed without departing from its scope. Furthermore, the foregoing description of the preferred embodiment of the invention and the best mode for practicing the invention are provided for the purpose of illustration only and not for the purpose of limitation—the invention being defined by the claims.

What is claimed is:

1. An elongate splint product for being dispensed in lengths suitable for a given medical use, comprising:
   (a) a multi-layer moisture-hardenable plaster substrate having first and second opposed major surfaces;
   (b) a soft cushion enveloping said first major surface and opposed marginal portions of said second major surface of said substrate and defining an exposed outermost surface layer of the splint product for residing directly against and protecting the skin of the wearer;
   (c) a moisture absorbent panel overlying said second major surface of said substrate and opposed marginal portions of said substrate and said cushions, said second major surface of said substrate and said moisture absorbent panel residing in contact with each other and defining a centrally-disposed moisture transfer channel for wicking away moisture from the substrate; and
   (d) first and second spaced-apart rows of stitches extending along the length of the splint product and through the marginal portions of said substrate, said cushion, and said panel to bind said substrate, cushion and panel together to form a unitary bandaging product which can be dispensed, cut to length, and applied without further assembly.

2. A medical splint product according to claim 1, wherein said cushion is folded to define spaced-apart opposed marginal portions overlying the marginal portions of the second major surface of said substrate and forms a centrally disposed moisture-transfer channel therebetween, and wherein said absorbent panel overlies the moisture-transfer channel and contacts the substrate to absorb and wick moisture away from the substrate.

3. A medical splint product according to claim 2, and including a row of center stitches extending along the length of the splint product through the absorbent panel and substrate in an area of the moisture-transfer channel for attaching the panel directly to the substrate.

4. A medical splint product according to claim 1, wherein said substrate comprises a plurality of knitted or woven fabric layers coated with plaster.

5. A medical splint product according to claim 1, wherein the moisture absorbent panel comprises cotton fibers.

6. A medical splint product according to claim 1, wherein said cushion is relatively thick as compared to said fabric panel.

7. A medical splint product according to claim 1, wherein said cushion comprises an elongate tubular sleeve enveloping the first and second major surfaces and opposed marginal portions of the substrate.

8. A medical splint product according to claim 1, wherein the width of the moisture absorbent panel is less than the width of the substrate.

9. A medical splint product according to claim 1, wherein the splint product is sufficiently flexible for packaging in roll form.

10. An elongate medical splint product for being dispensed in lengths suitable for a given medical use, comprising:
    (a) a multi-layer moisture-hardenable plaster substrate having first and second opposed major surfaces;
    (b) a soft cushion enveloping said first major surface and opposed marginal portions of the second major surface of said substrate, and defining an exposed outermost surface layer of the splint product for residing directly against and protecting the skin of the wearer; said cushion having corresponding opposed marginal portions overlying the opposed marginal portions of the second major surface of said substrate, and defining a centrally-disposed longitudinal moisture-transfer channel therebetween;
    (c) a moisture absorbent panel overlying said second major surface of said substrate and the opposed marginal portions of said cushion on the second major surface of said substrate and said moisture-transfer channel, said second major surface of said substrate and said moisture absorbent panel residing in contact with each other and defining a centrally-disposed moisture transfer channel for wicking away moisture from the substrate, said panel having a width less than the width of said substrate;
    (d) a center row of stitches extending along the length of the splint product through the absorbent panel and substrate in an area of the moisture-transfer channel for attaching the panel directly to the substrate; and
    (e) first and second spaced-apart side rows of stitches extending along the length of the splint product and through the marginal portions of said substrate, said cushion, and said panel to bind said substrate, cushion, and panel together to form a unitary bandaging product which can be dispensed, cut to length, and applied without further assembly.

* * * * *